United States Patent
Buechel et al.

(10) Patent No.: US 8,009,545 B2
(45) Date of Patent: Aug. 30, 2011

(54) OPTICAL RECORDING USING A WAVEGUIDE STRUCTURE AND A PHASE CHANGE MEDIUM

(75) Inventors: Dorothea Buechel, San Jose, CA (US);
Dieter Klaus Weller, San Jose, CA (US); Edward Charles Gage, Lakeville, MN (US); William Albert Challener, Eden Prairie, MN (US); Christophe Daniel Mihalcea, Newton (NZ)

(73) Assignee: Seagate Technology LLC, Scotts Valley, CA (US)

( * ) Notice: Subject to any disclaimer, the term of this patent is extended or adjusted under 35 U.S.C. 154(b) by 0 days.

(21) Appl. No.: 12/548,688

(22) Filed: Aug. 27, 2009

(65) Prior Publication Data
US 2010/0008208 A1    Jan. 14, 2010

Related U.S. Application Data

(62) Division of application No. 11/021,876, filed on Dec. 22, 2004, now Pat. No. 7,596,072.

(51) Int. Cl.
*G11B 7/135* (2006.01)
(52) U.S. Cl. .................................. 369/112.27
(58) Field of Classification Search ............. 369/112.27; G09B 7/109
See application file for complete search history.

(56) References Cited

U.S. PATENT DOCUMENTS

| | | | |
|---|---|---|---|
| 3,922,776 A | 12/1975 | Alger et al. | |
| 4,453,180 A | 6/1984 | Juergensen | |
| 4,750,806 A | 6/1988 | Biswas | |
| 4,771,415 A * | 9/1988 | Taki | 369/112.27 |
| 5,199,090 A | 3/1993 | Bell | |
| 5,218,584 A * | 6/1993 | Gfeller | 369/44.12 |
| 5,808,973 A | 9/1998 | Tanaka | |
| 5,835,458 A * | 11/1998 | Bischel et al. | 369/44.12 |
| 6,278,679 B1 | 8/2001 | Weiss et al. | |
| 6,307,827 B1 | 10/2001 | Nishiwaki | |
| 6,324,149 B1 | 11/2001 | Mifune et al. | |
| 6,376,827 B1 | 4/2002 | Kasama et al. | |
| 6,545,969 B1 | 4/2003 | Berg et al. | |
| 6,574,257 B1 | 6/2003 | Thronton et al. | |
| 6,680,900 B1 | 1/2004 | Takahashi et al. | |
| 6,724,718 B1 | 4/2004 | Shinohara et al. | |

(Continued)

FOREIGN PATENT DOCUMENTS

JP    03078124 A  *  4/1991

(Continued)

*Primary Examiner* — William J Klimowicz
*Assistant Examiner* — Mark L Fischer
(74) *Attorney, Agent, or Firm* — Robert P. Lenart, Esq.; Pietragallo Gordon Alfano Bosick & Raspanti, LLP

(57) ABSTRACT

An apparatus includes a component having a first surface, a first waveguide for directing electromagnetic radiation to a focal point adjacent to the first surface, a storage medium positioned adjacent to the first surface, a detector for detecting electromagnetic radiation reflected from the storage medium, and a structure positioned adjacent to the focal point for collecting the reflected electromagnetic radiation and for transmitting the reflected electromagnetic radiation toward the detector, wherein the structure comprises a second waveguide including a first cladding layer positioned adjacent to a first side of the first waveguide and having a first end positioned adjacent to the first surface and a second cladding layer positioned adjacent to a second side of the first waveguide and having a first end positioned adjacent to the air bearing surface.

15 Claims, 5 Drawing Sheets

U.S. PATENT DOCUMENTS

| | | | |
|---|---|---|---|
| 6,795,630 B2 | 9/2004 | Challener et al. | |
| 6,831,886 B1 * | 12/2004 | Yamasaki et al. | 369/112.28 |
| 6,885,627 B1 | 4/2005 | Taugher | |
| 6,980,374 B1 * | 12/2005 | Schlesinger | 359/726 |
| 7,068,883 B2 * | 6/2006 | Ludington et al. | 385/33 |
| 7,480,214 B2 * | 1/2009 | Challener et al. | 369/13.24 |
| 2001/0009541 A1 * | 7/2001 | Ueyanagi | 369/112.23 |
| 2001/0030938 A1 | 10/2001 | Oumi et al. | |
| 2001/0033546 A1 | 10/2001 | Katayama | |
| 2001/0055264 A1 | 12/2001 | Cheong et al. | |
| 2002/0001283 A1 | 1/2002 | Niwa et al. | |
| 2002/0006102 A1 | 1/2002 | Durnin et al. | |
| 2002/0011298 A1 | 1/2002 | Jain et al. | |
| 2002/0014575 A1 * | 2/2002 | Hatano et al. | 250/201.5 |
| 2002/0054560 A1 | 5/2002 | Boutaghou et al. | |
| 2002/0075784 A1 | 6/2002 | Kim | |
| 2002/0080709 A1 | 6/2002 | Park et al. | |
| 2002/0122376 A1 | 9/2002 | Song | |
| 2002/0150035 A1 | 10/2002 | Bernacki et al. | |
| 2002/0176349 A1 | 11/2002 | Gibson et al. | |
| 2003/0048744 A1 | 3/2003 | Ovshinsky et al. | |
| 2003/0072245 A1 | 4/2003 | Ueyanagi | |
| 2003/0099189 A1 | 5/2003 | Kim et al. | |
| 2003/0123335 A1 | 7/2003 | Rettner et al. | |
| 2003/0128633 A1 | 7/2003 | Batra et al. | |
| 2003/0184903 A1 | 10/2003 | Challener | |
| 2003/0206513 A1 * | 11/2003 | Watanabe et al. | 369/106 |
| 2004/0001394 A1 | 1/2004 | Challener et al. | |
| 2004/0001420 A1 | 1/2004 | Challener | |
| 2004/0001421 A1 | 1/2004 | Tawa et al. | |
| 2004/0008591 A1 | 1/2004 | Johns et al. | |
| 2004/0062503 A1 | 4/2004 | Challener | |
| 2004/0085861 A1 | 5/2004 | Hamann et al. | |
| 2005/0083826 A1 * | 4/2005 | Anatoliy et al. | 369/112.27 |
| 2006/0077787 A1 * | 4/2006 | Itagi et al. | 369/44.23 |

FOREIGN PATENT DOCUMENTS

| | | |
|---|---|---|
| JP | 2000-292338 | 10/2000 |
| JP | 2001-126282 | 5/2001 |
| JP | 2002-062479 | 2/2002 |

\* cited by examiner

OPTICAL RECORDING USING A WAVEGUIDE STRUCTURE AND A PHASE CHANGE MEDIUM

CROSS REFERENCE TO RELATED APPLICATION

This application is a divisional application of U.S. patent application Ser. No. 11/021,876, filed Dec. 22, 2004, and titled "Optical Recording Using a Waveguide Structure and a Phase Change Medium", now U.S. Pat. No. 7,596,072, which is hereby incorporated by reference.

STATEMENT REGARDING FEDERALLY SPONSORED RESEARCH OR DEVELOPMENT

This invention was made with United States Government support under Agreement No. 70NANB1H3056 awarded by the National Institute of Standards and Technology (NIST). The United States Government has certain rights in the invention.

FIELD OF THE INVENTION

This invention relates to data storage devices and more particularly to optical storage devices that utilize phase change storage media.

BACKGROUND OF THE INVENTION

Optical data systems rely on a beam of light to write and read information on a storage medium. There is a fundamental constraint—the diffraction limit—on how tightly the beam of light can be focused. This limit is directly related to the wavelength of the light. With a shorter wavelength, a smaller spot of light can be made and hence, more bits can be stored on a given area. The resolution limit is given by Abbe's equation:

Resolution=(Wavelength*0.61)/(Numerical Aperture).

Reduction of the size of the laser spot requires the use of a shorter wavelength laser and/or a higher numerical aperture lens. In going from CD to DVD to DVD-Blu-Ray, the numerical aperture was increased and the laser wavelength was decreased from 0.55 at 780 nm, to over 0.6 at 635 nm, and finally to 0.85 at 405 nm. Shorter wavelength light, as well as lenses of a higher numerical aperture (NA), produces focused spots with a smaller depth of focus (DOF) compared to systems using a longer wavelength and lower NA optics. The DOF can be expressed as follows:

$DOF = 2*\text{Wavelength}*(\text{Refractive Index})/(\text{Numerical Aperture})^2.$ Using optical far field techniques sub-diffraction-limit marks cannot be detected on a storage medium. In the most advanced DVD-Blu-Ray technique utilizing a NA of 0.85 and a wavelength of 405 nm, the smallest mark size is 140 nm. In addition, keeping the focal point at the right position with respect to the medium to record and read marks requires substantial effort by the servo system, since any disc wobbling and other imperfections during operation disturb the focal position.

There is a need to achieve an increase in data capacity in optical storage systems beyond that of DVD-Blu-Ray.

SUMMARY OF THE INVENTION

In a first aspect, the invention provides an apparatus including a component having a first surface, a first waveguide for directing electromagnetic radiation to a focal point adjacent to the first surface, a storage medium positioned adjacent to the first surface, a detector for detecting electromagnetic radiation reflected from the storage medium, and a structure positioned adjacent to the focal point for collecting the reflected electromagnetic radiation and for transmitting the reflected electromagnetic radiation toward the detector, wherein the structure comprises a second waveguide including a first cladding layer positioned adjacent to a first side of the first waveguide and having a first end positioned adjacent to the first surface and a second cladding layer positioned adjacent to a second side of the first waveguide and having a first end positioned adjacent to the air bearing surface.

In another aspect, the invention provides an apparatus including a component having a first surface, a phase change storage medium positioned adjacent to the first surface, a first waveguide for directing electromagnetic radiation to a focal point adjacent to the first surface for changing a phase of portions of the phase change storage medium using near field radiation, a first electrode having a first end positioned adjacent to the phase change storage medium, and a detector for detecting electrical current in the first electrode, wherein the electrical current changes in response to changes in electrical conductivity of the storage medium.

In another aspect, the invention further encompasses an apparatus including a phase change storage medium, a first electrode having a first end positioned adjacent to the phase change storage medium, and a detector for detecting electrical current in the first electrode, wherein the electrical current changes in response to changes in electrical conductivity of the storage medium.

DETAILED DESCRIPTION OF THE INVENTION

Figure 1:
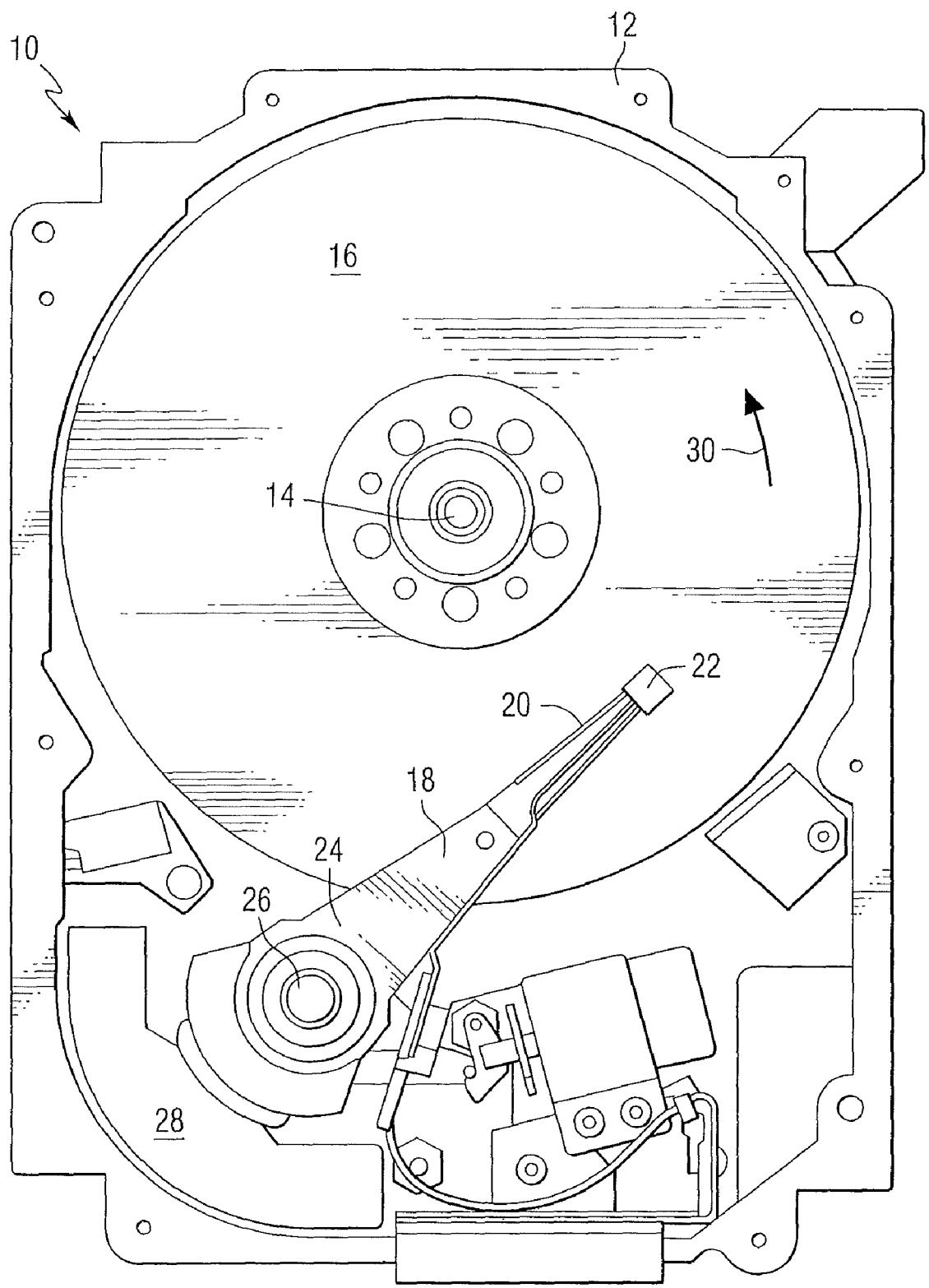
FIG. 1 is a pictorial representation of a disc drive that can include a recording head constructed in accordance with this invention.

Referring to the drawings, FIG. 1 is a pictorial representation of a head disc assembly portion of a disc drive 10 including a recording head that can be constructed in accordance with this invention. The disc drive includes a housing 12 (with the upper portion removed and the lower portion visible in this view) sized and configured to contain the various components of the disc drive. A spindle motor 14 is provided for rotating at least one data storage medium 16 within the housing. At least one arm 18 is contained within the housing 12, with each arm 18 having a first end 20 with a recording and/or reading head or slider 22, and a second end 24 pivotally mounted on a shaft by a bearing 26. An actuator motor 28 is located at the arm's second end 24, for pivoting the arm 18 about a pivot point to position the head 22 over a desired sector of the disc 16. The actuator motor 28 is regulated by a controller that is not shown in this view and is well-known in the art. The storage medium rotates in the direction indicated by arrow 30. As the disc rotates, the slider flies over the disc surface on an air bearing.

Figure 2:
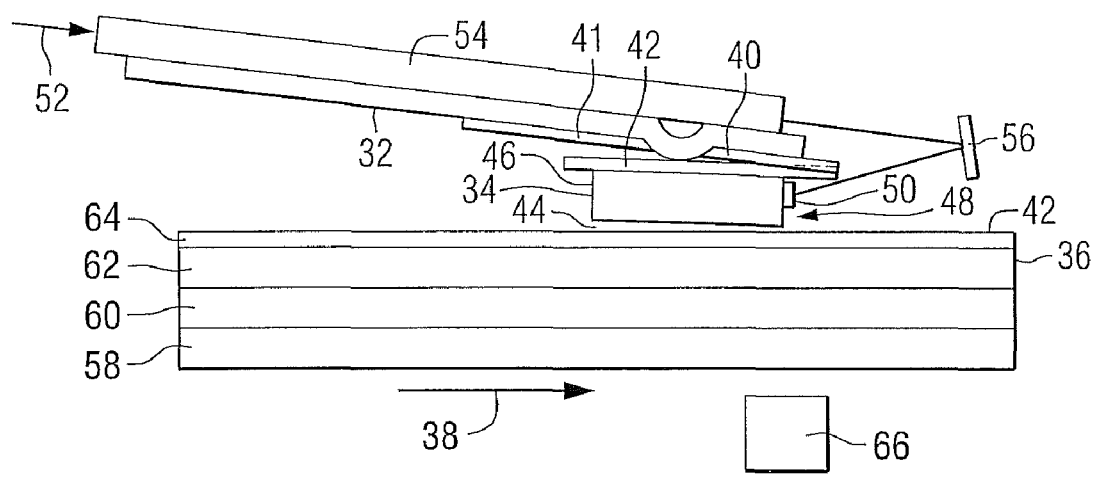
FIG. 2 is a schematic representation of an optical near field recording system using a slider with an integrated waveguide structure constructed in accordance with this invention.

FIG. 2 is a schematic representation of a portion of a suspension arm 32 and a component or slider 34, in combination with a recording disc 36. During writing and/or reading of data, the disc moves relative to the slider in a direction indicated by arrow 38. The slider is coupled to the suspension arm by a gimbal assembly 40, and is positioned adjacent to a surface 42 of the disc and separated from the surface of the disc by an air bearing 44. The gimbal assembly includes a first portion 41 connected to the suspension arm 32 and a second portion 42 connected to the slider 34. The second portion is cantilevered to the first portion. The slider has a leading, or front, end 46 and a trailing, or back, end 48. In this example, the leading end faces toward the pivot point of the suspension arm and the trailing end faces away from the pivot point of the suspension arm. The slider includes an optical structure in the form of a solid immersion mirror 50 mounted adjacent to the trailing end. A laser produces a beam of light, illustrated by arrow 52, that is transmitted toward the slider by an optical fiber 54. A mirror 56 is mounted at the end of the suspension arm to reflect the light toward the optical transducer. A grating can be used to couple the light into the solid immersion mirror. The recording disc in this example includes a substrate 58, one or more sublayers 60, a recording layer 62 that includes a phase change material, and one or more cover layers 64. A detector 66 can be positioned under the disc to detect light transmitted through the disc.

For optical recording, an electromagnetic wave of, for example, visible, infrared or ultraviolet light is directed onto a surface of a data storage medium to raise the temperature of a localized area of the medium and create phase changes in the recording layer of the storage medium. To read data from the storage medium, light can be directed onto the medium and either light reflected from the medium or light transmitted through the medium can be detected. Marks in the phase change material will affect a property of the reflected or transmitted light, and a change in the affected property can be used to indicate the presence or absence of a mark on the medium.

The recording layer can include an active film material such as a write-once or rewritable phase change material; organic dyes as applied in write once, read many times (WORM); or any other material that changes properties upon light irradiation/heating, for example, magneto-optic material.

Optimal active media include phase change alloys such as group VI, group V and group III elements. These alloys undergo a phase transition from amorphous to crystalline (stable condition) or vise-versa upon heating. Specific examples are Ge—Sb—Te alloys (nucleation dominated crystallization), or Ag—In—Sb—Te (growth dominated crystallization), as used in DVD products. Growth-dominated, doped SbTe eutectic alloys are suitable for small mark sizes, since their crystallization time decreases with decreasing mark size. It has been shown that such phase change media have the capability to hold stable amorphous marks with sizes below 100 nm.

When phase change materials are deposited by vacuum techniques at room temperature, the as-deposited state is amorphous and meta-stable. To convert the material to a crystalline stable state, it needs to be initialized (optically or thermally). For effective heat management in the disc stack, in addition to the active film, dielectric and metals films can be added. A dielectric spacer and capping layer can be formed of $ZnS-SiO_2$, a material with an especially thermostable structure, that allows a high number of read-write cycles. In cases where read out is done using reflected light, an Al—Cr alloy heat sink and reflection layer can be added. The substrate material can be, for example, glass or polycarbonate. The medium can be post-sputter processed to assure the required smoothness for flying a slider over the surface of the medium.

The recording layers contain spiral tracks of mark patterns that differ in reflectivity from the area between marks. As the focused laser beam passes over a mark, changes in the light level can be detected in transmission or reflection. In the reflective mode, light is coupled back into the waveguide structure and coupled out to a detector. In the transmission mode, a light collecting lens and a detector are positioned at the opposite side of the disc. The detector current, which is representative of the mark pattern, is decoded to produce digital information.

To write to the media, a short, high power laser pulse (usually on the order of nanoseconds) is applied to the media, to produce amorphization of the initialized, crystalline media. To erase the media, a longer, low power pulse (on the order of microseconds) is applied to the media, to re-crystallize a portion of the media and erase the data stored on that portion of the media. The temperature for amorphization is about 600° C., and the temperature for crystallization is about 200° C.

The phase change materials exhibit different optical constants depending on their phase: crystalline or amorphous. Changes between the phases are laser light induced and the mark size is limited by a fundamental constraint—the diffraction limit—given by Abbe's equation:

$$\text{Resolution} = (\text{Wavelength} * 0.61)/(\text{Numerical Aperture}).$$

However, optical far field techniques have been reported that enable writing with marks having sizes below the diffraction limit in such recording materials, using for example the so-called super resolution effect. The limiting factor in optical data storage is the ability to read back such small marks with a sufficient carrier-to-noise ratio (CNR) but without destroying information by applying an excessive readout laser power.

Figure 3:
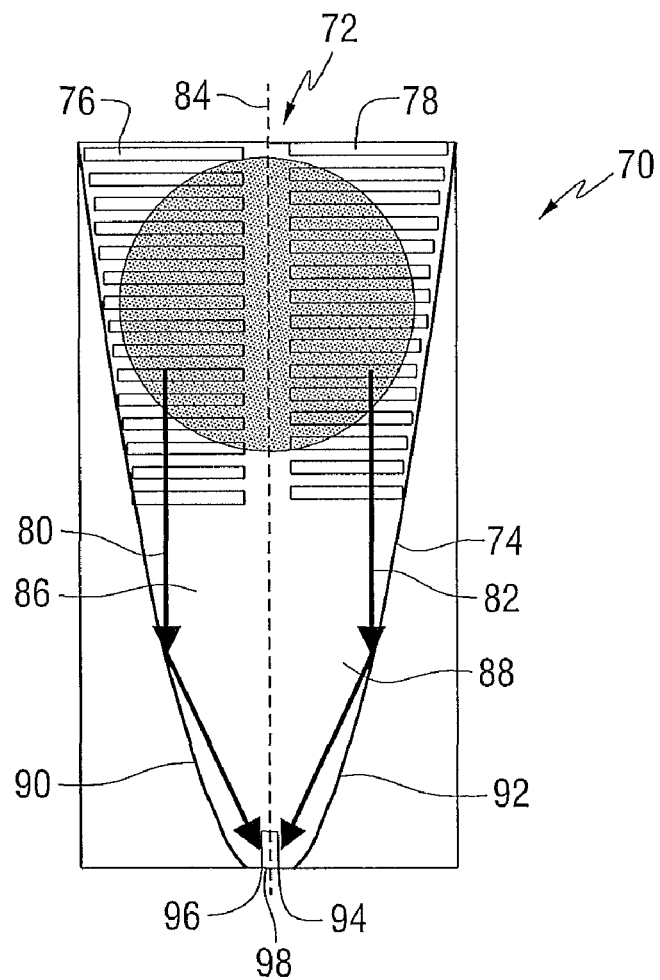
FIG. 3 is a schematic representation of a solid immersion mirror structure.

FIG. 3 is a schematic representation of a solid immersion mirror structure 70. The solid immersion mirror includes a planar waveguide 72 shaped in the form of a parabolic mirror (also called a condenser) 74. A first grating 76 and a second grating 78 form a split grating for coupling incident light into a waveguide. Electromagnetic radiation in the form of polarized light, illustrated by arrows 80 and 82 is directed onto the gratings. The gratings are offset in a direction parallel to the longitudinal axis 84 of the waveguide, so that the coupled light entering one half 86 of the waveguide is shifted by 180° with respect to light entering the other half 88 of the waveguide. The waveguide is constructed of materials, which provide interfaces at the sides 90 and 92 to reflect the light. The sides 90 and 92 of the waveguide are shaped such that the light is brought to a focus at a focal point 94. A metallic transducer 96 is positioned at the focal point. The transducer is preferably made of a metal such as gold, silver, aluminum, or copper.

The solid immersion mirror structure is able to focus the light into a sub-wavelength spot for optical near field recording on phase change media. The structure can be fabricated on a slider, similar to that used in magnetic hard drives, that flies at a distance on the order of the optical near field over a phase change storage medium to optically write marks with sizes far below the diffraction limit.

In FIG. 3, the condenser is a planar solid immersion mirror (P-SIM). Because of the phase difference between the light in the two halves of the waveguide at the focal point, the electric field of the light is polarized in the longitudinal direction, which is along the axis of symmetry of the condenser. The longitudinal electric field couples strongly to the transducer when it is oriented in the longitudinal direction. The end 98 of the solid immersion mirror can be positioned adjacent to the storage medium, such that electromagnetic radiation emitted at the end of the transducer can be used to heat a portion of the medium. If the transducer is chosen with the correct dimensions, particularly the correct length, then it resonates with the incident light and creates extremely large electric fields in a medium in the vicinity of the end of the transducer.

Light from a laser diode is coupled by the gratings into the planar waveguide structure, which can include a core layer on a $SiO_2$ cladding. The sides of the waveguide can have a parabolic shape to focus the light power into a spot having dimensions depending on the waveguide stack structure and the materials used. Spot sizes of 180 nm (cross-track) by 130 nm (in-track) have been demonstrated for a SIM structure with an effective refractive index of about 1.6, using a 633 nm laser diode.

In one example, using a 405 nm laser diode and a $TiO_2$ core layer material, with an effective refractive index of 1.8, the spot size can be scaled down to 107 nm (cross-track) by 77 nm (in-track) to provide a recording density of about 140 $Gb/inch^2$. DVD-Blu-Ray uses spot sizes of 280 nm and achieves a density of about 19.5 $Gb/inch^2$. Thus, the areal density improvement of an optical near field recording setup using a slider with integrated waveguide structure could be a factor of 7 compared to DVD-Blu-Ray. A pin made out of an appropriate metal, placed at the focal point of the waveguide parabola (as shown in FIG. 3) can confine the light spot to below 100 nm.

Figure 4:
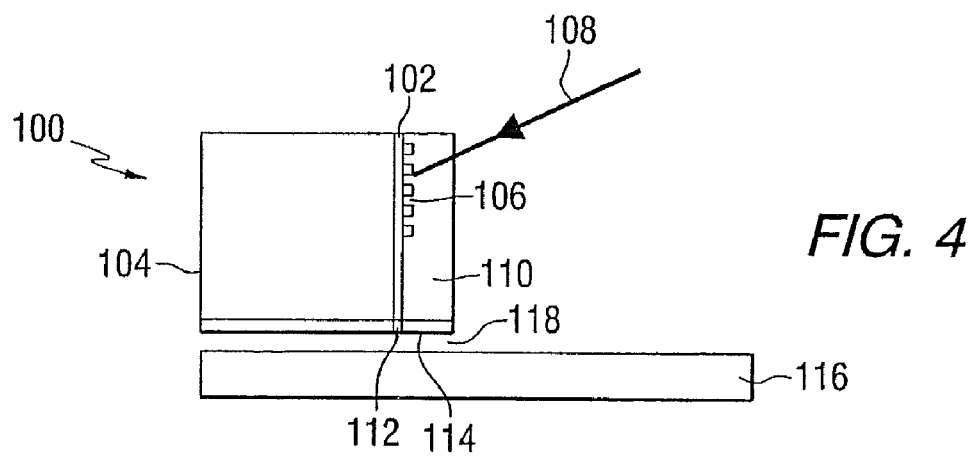
FIG. 4 is a schematic representation of a portion of a slider including a solid immersion mirror structure.

FIG. 4 is a schematic representation of a portion of a component or slider 100 including a solid immersion mirror structure. A solid immersion mirror structure 102 is attached to a body 104 of the slider. The solid immersion mirror structure includes a parabolic shaped planar waveguide and cladding layers positioned on opposite sides of the core layer. A grating 106 is provided to couple light 108 into the waveguide. An additional transparent layer 110, which can be alumina, is positioned over the solid immersion mirror structure. A metal pin 112 is positioned at the focal point of the waveguide adjacent to the air bearing surface 114 of the slider. A phase change storage medium 116 is separated from the slider by the air bearing 118.

Figure 5:
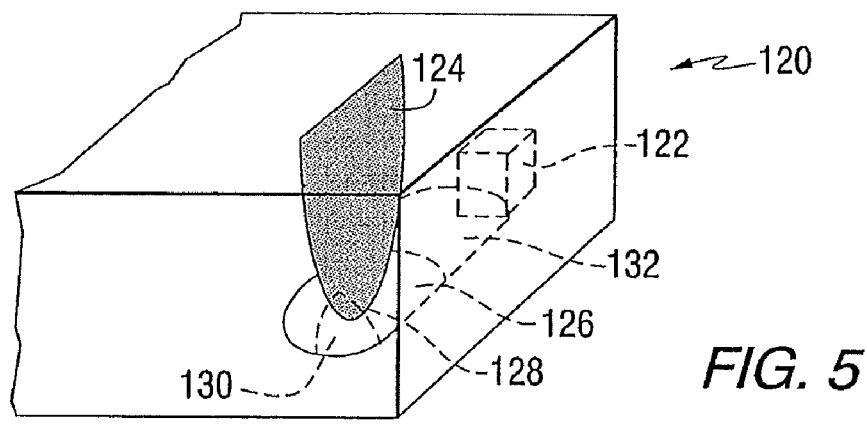
FIG. 5 is an isometric view of a portion of a slider including a solid immersion mirror structure.

To read data from the storage medium, light is directed onto the storage medium and the reflected light from the marks on the recording disk is detected. Marks in the storage medium cause changes in the properties of the reflected light, such as a change in intensity. FIG. 5 is an isometric view of a portion of a component or slider 120 including a detector 122 and means for directing the reflected light from the marks on the media toward the detector. Since the light reflected from the recorded bits is scattered in several directions and is thus very weak (see FIG. 8), a reflecting cavity or indentation collects the scattered light and redirects it to a detector. In more detail, a notch, indention, or depression 126 is formed in the air bearing surface of the slider around the end 128 of the solid immersion mirror structure. The internal surface 130 of the notch, indention, or depression 126 is shaped to direct the reflected light along a waveguide 132 to the detector. The waveguide 132 can include a material having a higher refractive index than that of the surrounding material so that light travels along the waveguide by total internal reflection. Alternatively, the light can travel to the detector through air.

The example of FIG. 5 places a half parabolic indent with a joined waveguide at the ABS. This mirror collects the scattered light and guides it into one common direction facilitating the detection of the weak scattered light. This direction can be along any suitable axis along the ABS surface depending upon the location of the detector. The detector can be integrated into the slider or placed outside the drive. The cavity should have dimensions of several microns (several wavelengths) to allow visible light to be guided to a detector placed at a convenient location. The shape of the cavity mirror surface is tailored to channel the scattered light effectively in the chosen direction.

The waveguide can have metallized sidewalls to reflect the light into the desired direction or it can be a dielectric waveguide including a lower index outer cladding layer and a high index core layer such that the light is transported in a lossless manner via total internal reflection to the detector.

Figure 6:
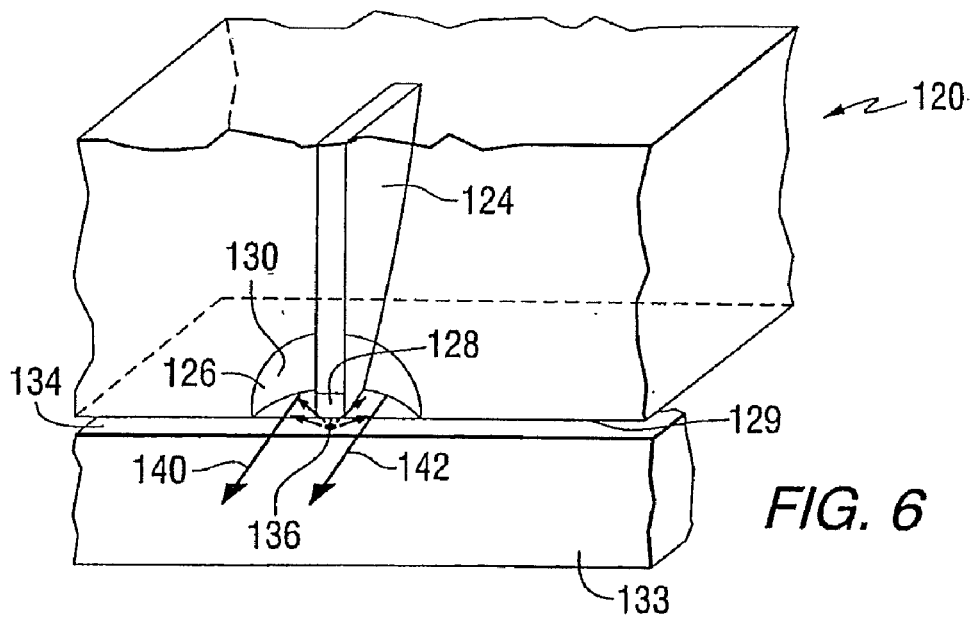
FIG. 6 is an isometric view of a portion of the slider of FIG. 5.

FIG. 6 is an isometric view of a portion of the slider 120 of FIG. 5 including a solid immersion mirror structure. The solid immersion mirror structure 124 is embedded in the slider. The solid immersion mirror structure includes a parabolic shaped planar core layer and cladding layers positioned on opposite sides of the core layer. A metal pin 128 is positioned at the focal point of the waveguide adjacent to the air bearing surface 129 of the slider. A phase change storage medium 133 is separated from the slider by the air bearing 134. The indention 126 is formed in the air bearing surface of the slider around the end 136 of the solid immersion mirror structure. The internal surface 130 of the indention 126 is shaped to reflect the reflected light in the direction indicated by arrows 140 and 142 along the waveguide. A detector can be mounted to sense the reflected light, and can be coupled to the indention 126 via the waveguide. The channel indentation leading to the detector is not shown in FIG. 6 but would be positioned to transmit light indicated by arrows 140 and 142 toward the detector.

Figure 7:
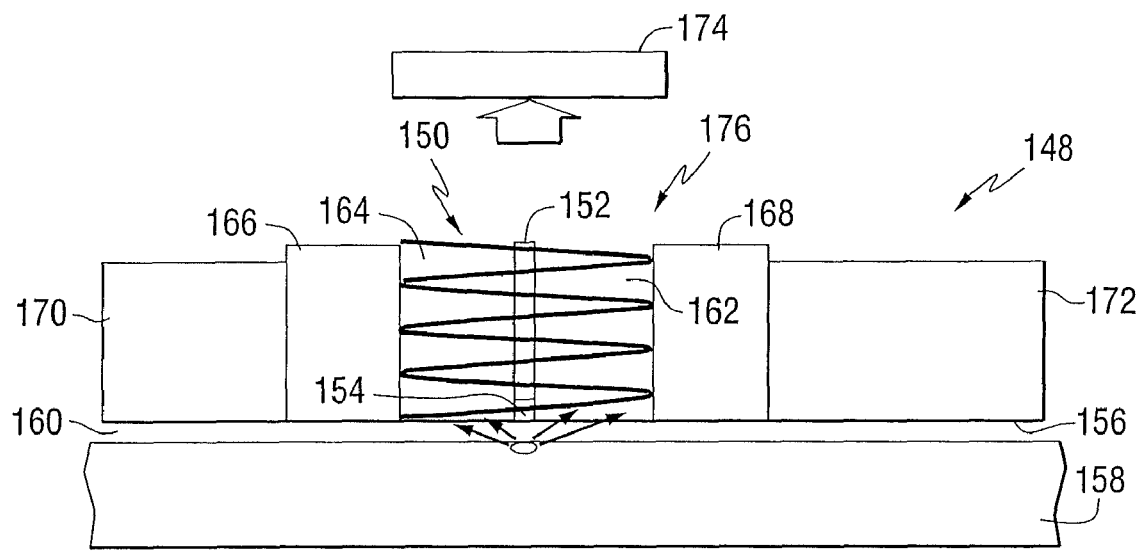
FIG. 7 is a schematic representation of a portion of another slider constructed in accordance with this invention.

Alternatively, the light can be detected at the top side of the slider. In the example of FIGS. 5 and 6, the SIM includes a high index core material such as tantala or titania and a cladding with a lower refractive index, e.g. aluminum oxide. The SIM can be embedded in a further film with a tuned, lower refractive index, e.g. glass, to form a multimode waveguide. Then the scattered light can be redirected back into the multimode waveguide structure. The detection of the scattered light would then be possible from the top side of the slider using the power coupling mechanism in a reversed way. FIG. 7 illustrates this concept.

FIG. 7 is a schematic representation of a portion of another component or slider 148 constructed in accordance with this invention. A solid immersion mirror structure 150 is embedded in the slider. The solid immersion mirror structure includes a parabolic shaped core layer 152 and cladding layers 162 and 164 positioned on opposite sides of the core layer. A metal pin 154 is positioned at the focal point of the waveguide adjacent to the air bearing surface 156 of the slider. A phase change storage medium 158 is separated from the slider by the air bearing 160. The solid immersion mirror structure 150, which can be alumina, is positioned between cladding layers 166 and 168, which can be glass. In one example, the core layer 152 can have an index of refraction of about 2, the cladding layers 162 and 164 can have an index of refraction of about 1.6, and the cladding layers 166 and 168 can have an index of refraction of about 1.4. This forms a multimode waveguide 176 that is embedded in the slider as illustrated by material 170 and 172, which can be for example AlTiC. Light emitted at the pin 154 is reflected from the storage medium 158 and coupled into the multimode waveguide 176. The surface of the end of the waveguide 176 can be modified to improve the coupling of light into the end of the waveguide. An antireflection coating (AR) can be applied to the top surface of the slider. The thickness of the AR layer can be adjusted such that light that is traveling up the waveguide is not reflected back into the waveguide at this interface, but is coupled out of the waveguide in a direction toward the detector. The same is true for the ABS side of the slider. A well chosen AR coating can effectively help to couple light, reflected from the storage medium, back into the outer waveguide structure. A detector 174 is positioned to detect light transmitted through waveguide 176.

FIG. 7 shows a cross-section of a SIM including core 152 and cladding layers 162 and 164, that are further embedded in a glass film 166 and 168. The low index glass film works as a cladding for the alumina core 152 and cladding layers 162 and 164 to form a multimode waveguide. This considerably wider waveguide directs back-scattered light from the sample, independent of its angle of incidence, to the detector 174, which can be placed on top of the SIM. The physical dimensions of the alumina/glass multimode waveguide at the ABS are much larger than that of the original SIM.

Figure 9:
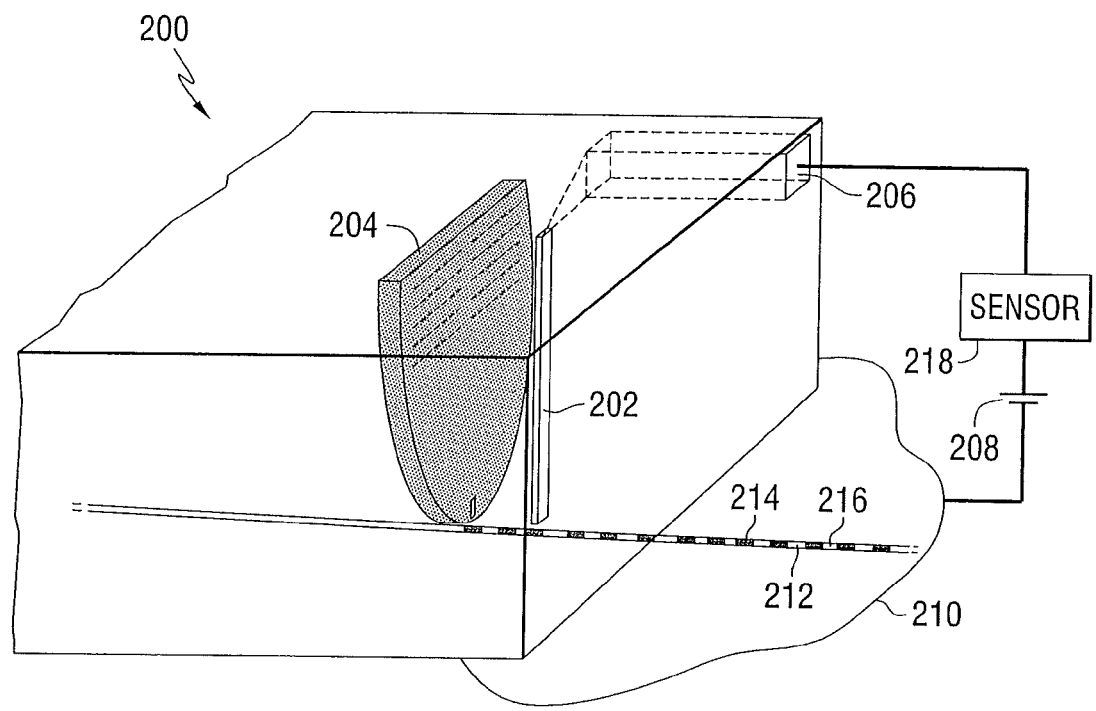
FIG. 9 is a schematic representation of a portion of another slider constructed in accordance with this invention.

The readout function can alternatively detect resistivity changes to differentiate between amorphous and crystalline areas in phase change films, for instance, by use of a different part of the slider. To detect resistivity changes, the slider could include an embedded conducting sensor. One could then measure a current flowing from the slider into the phase change marks or out of them if the disc structure is appropriately adjusted. Due to the difference in conductivity between amorphous and crystalline marks, the signal is generated. FIG. 9 is a schematic representation of a portion of a component or slider 200, which includes an electrode or wire 202 that can be used to read data from a phase change media. The slider 200 includes a waveguide 204 that is similar to the waveguides described above. The electrode 202 is electrically connected to a bonding pad 206, which serves as a connection to an external voltage source 208. In this example, the voltage source is connected between the bonding pad and the storage medium 210. An example recording track 212 is shown to be positioned under the slider. The track contains amorphous marks 214 and crystalline portions 216 that have different electrical conductivities. When a voltage is applied between the electrode 202 and the medium 210, electrons tunnel between the electrode and the medium. The electron tunneling density will increase or decrease depending upon whether the electrode is over a semimetallic area or a less conductive area of the medium. A sensor 218 can be placed in the circuit to detect changes in electrical current that are representative of changes in electron tunneling density. These current changes are then representative of the data stored on the storage medium.

In another example, the slider could include two electrodes spaced by a small gap (~10 nm or so) on the air bearing surface. Then the resistivity between them could be measured as the slider flies over the surface of the disc. Some electrons would tunnel out of one electrode, into the medium, and then back into the other electrode if a sufficient electrical potential was placed between the two electrodes. The amount of tunneling current would then determine whether the medium adjacent to the gap was amorphous or semimetallic.

Figure 10:
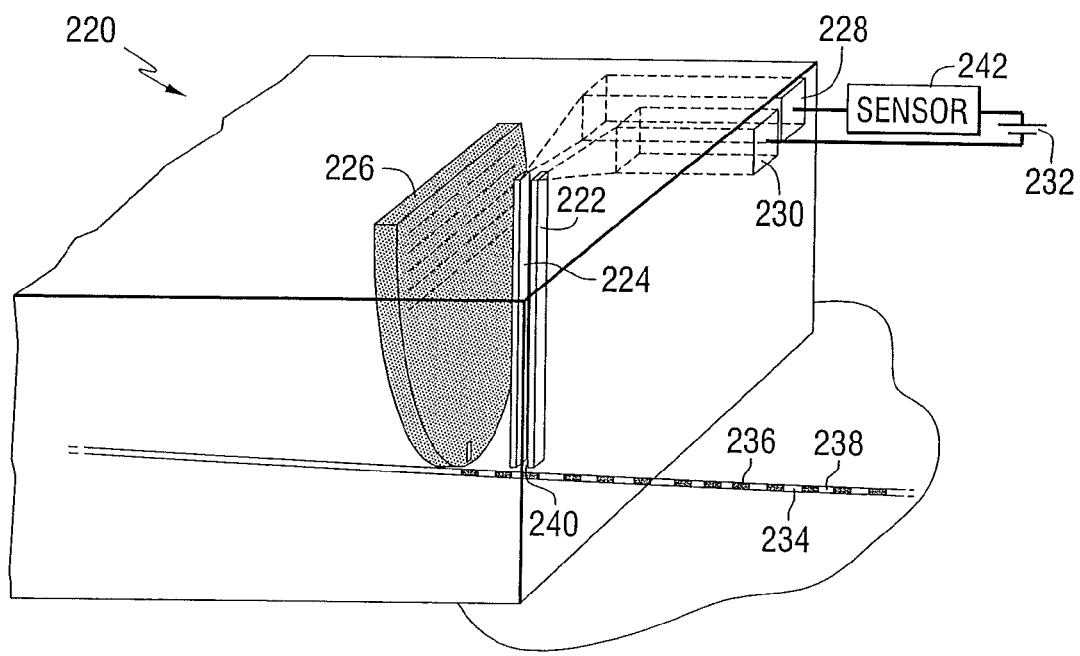
FIG. 10 is a schematic representation of a portion of another slider constructed in accordance with this invention.

FIG. 10 is a schematic representation of a portion of a component or slider 220, which includes two electrodes or wires 222 and 224 that can be used to read data from a phase change media. The slider 220 includes a waveguide 226 that is similar to the waveguides described above. The electrodes 222 and 224 are electrically connected to bonding pads 228 and 230, which serves connections to an external voltage source 232. In this example, the voltage source is connected between the bonding pads. An example recording track 234 is shown to be positioned under the slider. The track contains amorphous marks 236 and semimetallic portions 238 that have different electrical conductivities. The electrodes are separated by a gap 240 adjacent to the air bearing surface. When a voltage is applied between the electrodes 222 and 224, electrons tunnel between one of the electrodes and the medium, and between the medium and the other electrode. The electron tunneling density will increase or decrease depending upon whether the electrodes are over a semimetallic area or a less conductive area of the medium. A sensor 242 can be placed in the circuit to detect changes in electrical current that are representative of changes in electron tunneling density. These current changes are then representative of the data stored on the storage medium.

The distance between the ends of the electrodes, that are adjacent to the storage medium, must be in the same order as the mark size, which can be in the range of 5 to 7 nm, or smaller. The width of the ends of the electrodes in the down track direction can be in the order of less than 20 nm. The electrodes can be constructed of, for example, tungsten. Alternative shapes can also be used for the electrodes. For example the electrodes can be sharpened near the air bearing surface of the slider.

This invention can also address the problem of limited resolution in defect detection with an optical disc inspection tool. Future magnetic data storage densities aiming for TB/in$^2$ require a reduced flight height of the recording head on the order of a few nanometers. Such low flight heights demand improved substrate quality and media coating processes to assure maximum cleanliness and smoothness as well as media homogeneity on a sub-nanometer scale. To control these properties during production and for testing of finished discs, novel and fast inspection tools rendering sub-nanometer resolution are necessary.

A known optical method of identifying particles and defects on media and metal or glass substrates, is scanning micro-ellipsometry combined with scatterometry, whereby defects are detected as regions with deviating optical properties when illuminated with a focused laser beam. Small contaminants or defects are usually detected via their scattering properties that strongly depend on the material and the size of the defect. One currently available inspection tool using a 405 nm laser in a far field arrangement can detect defects of only 100 nm dimensions. For such far field techniques the resolution is principally diffraction limited to about half the wavelength of the light according to Abbe's equation: Resolution=(Wavelength*0.61)/(Numerical Aperture). As a result, any size and shape information for contaminants with dimensions below the diffraction limit is lost. Although, such small particles can still be detected in the far field under favorable conditions, they can only be identified as point scatterers but not resolved individually if they are spaced apart by a distance less than approximately half the wavelength.

A SIM based head has been suggested to be used as the illuminating sensor in the near field to improve the optical resolution of a spin stand based inspection tool. The SIM based head provides an optical spot at the ABS with arbitrary small dimensions. The spot dimensions at the ABS are primarily determined by the dimensions of a small metal structure inside the head that is illuminated with light of a suitable polarization. Theoretically such a spot could be as small as 20 nm. The metal structure works as a strong absorber of the incident light and converts the incident optical field into a surface plasmon polaritron. On the media side, the spot dimensions depend additionally on the flight height of the head, which can be adjusted to a desired value. Such an "optical head" can be used to investigate and characterize the surfaces of glass and metal substrates as well as finished media discs with respect to defects and contaminations by exploiting the increased optical resolution of the SIM based optical slider.

FIG. 6 depicts a slider with the optical components necessary to achieve the desired sub-wavelength resolution. A dielectric waveguide transports power, which is coupled in at the top-side of a parabolic guiding layer (by suitable means) to the metal pin at the ABS surface. The transported light is focused into the focal point of the parabola, which is placed at the ABS level of the slider. The slider can be mounted on a suspension to fly at an appropriate height above the sample to illuminate particles and defects on the disc under investigation.

The detection of light scattered from the sample can be carried out in several ways. For transparent substrates (glass, plastics etc.) the detection of scattered light can be performed in transmission by using conventional high NA collimating optics at the backside of the substrates to collect as much light as possible and to direct it to a detector. For opaque substrates such as metal discs or glass discs coated with a recording layer, the scattered light intensity can be measured in reflection.

The air bearing surface (ABS) of the recording head in the region surrounding the SIM can be modified to include another mirror or lens structure as illustrated in FIGS. 5 and 6 to collect and channel the backscattered light from the substrate to a detector.

Figure 8:
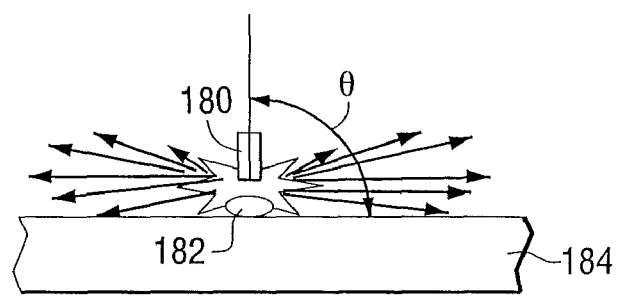
FIG. 8 is a schematic representation of light scattering by a particle on the surface of a recording medium.

FIG. 8 is a schematic representation of light scattering by a particle on the surface of a recording medium. The optical properties of the illuminating near field transducer (pin) 180 bring about that the interaction with a defect 182 on the substrate 184, e.g. a dielectric particle. This leads to a collective light scattering at certain angles (cos 2θ) around the defect as shown by the arrows in FIG. 8.

The near field writing and reading technique of this invention uses a slider with an integrated waveguide structure in combination with a phase change medium to provide high data capacity (beyond DVD-Blu-Ray) with advantages like stability of focus, removability, low cost and compatibility with ROM distribution formats.

This invention provides an apparatus and method for optical near field recording. The apparatus can be used on phase change material discs to write, and to allow the readback of small marks. The apparatus can include a phase change medium and a slider with an integrated waveguide structure.

In the described examples, the waveguide structure is a solid immersion mirror. However, other waveguide structures can also be used in the apparatus of this invention. For example, a mode index lens structure can be used and a metal pin can be placed at the focal point of the mode index lens. Alternatively, three-dimensional waveguide structures could be used.

While the invention has been described in terms of several examples, it will be apparent to those skilled in the art that various changes can be made to the disclosed examples without departing from the scope of the invention as defined in the following claims.

What is claimed is:

1. An apparatus comprising:
   a component having a first surface;
   a solid immersion mirror waveguide having a first end adjacent to the first surface and including a core layer and first and second cladding layers positioned on opposite sides of the core layer, the core layer including sides shaped to direct electromagnetic radiation to a focal point adjacent to the first surface;
   a storage medium positioned adjacent to the first surface; and
   a second waveguide including the first and second cladding layers, a third cladding layer positioned adjacent to the first cladding layer and on an opposite side of the first cladding layer with respect to the core layer, and a fourth cladding layer positioned adjacent to the second cladding layer and on an opposite side of the second cladding layer with respect to the core layer, the second waveguide having a first end positioned adjacent to the first surface.

2. The apparatus of claim 1, wherein the storage medium comprises:
   a phase change medium.

3. The apparatus of claim 1, further comprising:
   a detector for detecting electromagnetic radiation reflected from the storage medium.

4. The apparatus of claim 1, wherein the core layer is a parabolic-shaped core layer.

5. The apparatus of claim 4, wherein the core layer comprises alumina.

6. The apparatus of claim 5, wherein the first and second cladding layers comprise glass.

7. The apparatus of claim 1, further comprising:
   a first antireflective coating on a first end surface of the second waveguide.

8. The apparatus of claim 7, further comprising:
   a second antireflective coating on a second end surface of the second waveguide.

9. The apparatus of claim 1, further comprising:
   a metallic pin positioned at the focal point for concentrating near field electromagnetic radiation near a surface of the storage medium.

10. The apparatus of claim 1, wherein the first surface is an air bearing surface.

11. The apparatus of claim 1, wherein the electromagnetic radiation reflected from the storage medium passes through the second waveguide.

12. The apparatus of claim 1, wherein the core layer has a first index of refraction, the first and second cladding layers have a second index of refraction lower than the first index of refraction, and the third and fourth cladding layers have a third index of refraction lower than the second index of refraction.

13. The apparatus of claim 12, wherein the first index of refraction is about 2, the second index of refraction is about 1.6, and the third index of refraction is about 1.4.

14. The apparatus of claim 1, wherein the second waveguide is wider than the solid immersion mirror waveguide.

15. The apparatus of claim 1, wherein the second waveguide is a multimode waveguide.

* * * * *